(12) United States Patent
Toda

(10) Patent No.: US 6,585,674 B2
(45) Date of Patent: Jul. 1, 2003

(54) DEVICE AND METHOD FOR TREATING ARTHRITIS OF KNEE

(76) Inventor: Yoshitaka Toda, 14 -1 Toyotsu-cho, Suita, Osaka (JP), 564-0051

( * ) Notice: Subject to any disclaimer, the term of this patent is extended or adjusted under 35 U.S.C. 154(b) by 0 days.

(21) Appl. No.: 09/823,607

(22) Filed: Mar. 28, 2001

(65) Prior Publication Data

US 2001/0047146 A1 Nov. 29, 2001

(30) Foreign Application Priority Data

Apr. 5, 2000 (JP) ........................................ 2000-103669

(51) Int. Cl.$^7$ ................................................. A61F 5/00
(52) U.S. Cl. ............................ 602/62; 602/66; 128/876
(58) Field of Search ............................. 602/23, 27, 28, 602/60, 65, 66; 128/869, 882, 876

(56) References Cited

U.S. PATENT DOCUMENTS

| | | | | |
|---|---|---|---|---|
| 1,577,203 A | * | 3/1926 | Cramer | 602/66 |
| 2,358,966 A | * | 9/1944 | Einstoss | 602/66 |
| 2,633,130 A | * | 3/1953 | Scholl | 602/66 |
| 3,086,520 A | * | 4/1963 | Scholl | 602/66 |

OTHER PUBLICATIONS

Sasaki, T, et al; Clinical Evaluation of the Treatment of Osteoarthritic Knees Usin a Newly Designed Wedged Insole, (Aug. 1987), Clinical Orthopaedics and Relate Research, No. 221, pp. 181–187.

Yasuda, K, et al; The Mechanics of Treatment of the Osteoarthritic Knee with a Wedged Insole, (Feb. 1987), Clinical Orthopaedics and Related Research, No. 215; pp. 162–172.

Keating, EM, et al; Use of Lateral Heel and Sole Wedges in the Treatment of Medial Osteoarthritis of the Knee, Aug. 1993, Orthopaedic Review, pp. 921–924.

Pollo, FE, Bracing and Heel Wedging for Unicompartmental Osteoarthritis of the Knee, Winter 1998, American Journal of Knee Surgery; vol. 11, No. 1, pp. 47–50.

Tohyama, H, et al., Treatment of osteoarthritis of the knee with heel wedges, 1991, International Orthopaedics, vol. 15, No. 1, pp. 31–33.

Vaes, P, et al., Objective Roetgenologic Measurements of the influence of Ankle Braces on Pathologic Joint Mobility. A Comparison of 9 Braces, 1998, Acta Orthopaed Belgiva, vol. 84–2, pp. 201–209.

* cited by examiner

*Primary Examiner*—Michael A. Brown
(74) *Attorney, Agent, or Firm*—Nancy Lord Johnson, Ltd.

(57) ABSTRACT

The present invention relates generally to a therapeutic device and related methods for treating arthritis of the knee. The therapeutic device includes a stretchable band having a predetermined length, a flexible and resilient body installed in the longitudinal middle of the stretchable band with a substantially triangular cross-section whose height is greater at one side of the stretchable band than at the other, such that the higher portion of the flexible and resilient body is applied to the sole at a position nearer to the inner or outer side thereof, and the stretchable band may be used to wrap and fix the ankle.

20 Claims, 6 Drawing Sheets

Mean Value of Change in the Talocalcaneal Angle

2. Difference in the Talocalcaneal Angle
3. Present Invention
4. Conventional sole plate (new)
5. Conventional sole plate (after one year)

Mean Value of the Correction Angle of the Knee

2. Difference in Knee Correction
3. Present Invention
4. Conventional sole plate

DEVICE AND METHOD FOR TREATING ARTHRITIS OF KNEE

FIELD OF THE INVENTION

The present invention relates to a therapeutic device for treating arthritis of the knee, including osteoarthritis of the knee.

BACKGROUND

Osteoarthritis of the knee commonly begins with cartilage degeneration secondary to varus deformity that is multifactorial and often age-related. Varus deformity, whether or not age related, disturbs the positional relationship between the femur and tibia, resulting in partial wear and gradual loss of elasticity of the cartilage between the femur and the tibia. This causes local pressure directly on the bone and consequent bony proliferation at the joint edge and deformity. Overwork may wear or partly wear the joint due to its inherent disorder and similar proliferative change at the joint edge and the induction of osteoarthritis.

Osteoarthritis has been treated with an insole known as a sole plate. For an insole to function as a therapeutic device, the right or left side is higher than the opposite side.

For a patient with osteoarthritis of the knee caused by varus deformity, the lateral portion of the insole is higher than the medial portion, so as to raise the lateral sole and correct the varus deformity. By correcting the varus deformity, the unequal compression and tensile forces upon the knee are more evenly distributed. Although this more or less alleviates pain and other symptoms of arthritis of the knee, the level of treatment attained remains far less than clinically satisfactory.

Shortcomings of the conventional sole plate, in addition to the less than satisfactory therapeutic effect, include the following:
(1) The insole is difficult to use while wearing open-toed shoes, high-heels and after removing shoes at home.
(2) Because the insole is placed into a shoe when in use, it may become displaced causing a loss of therapeutic effect or the appearance of a reverse effect.
(3) The insole may cause a foul odor of the shoe or foot.
(4) Generally, a conventional insole is produced using a prepared mold and is often expensive. Because of its price, the user often continues to use the insole even if it wears somewhat, a condition that not only reduces its therapeutic effect but also risks the appearance of a reverse effect and aggravation of symptoms.

OBJECTS OF THE INVENTION

The present invention has been accomplished with the above in mind. The inventor has discovered a relatively inexpensive, therapeutic device for the treatment of arthritis of the knee that exerts a superior therapeutic effect on arthritis of the knee and can be used with and without shoes, and which is stable without the possibility of positional deviation and does not cause a foul odor of the shoe or foot.

SUMMARY OF THE INVENTION

The present invention relates to the treatment of arthritis of the knee by fixing the ankle while raising the lateral or medial sole. The inventor has now discovered that by combining ankle fixation and the prior practice of raising the lateral or medial sole, a synergistic improvement may be obtained in patients with arthritis of the knee.

In a preferred embodiment, the therapeutic device of the present invention comprises a stretchable band of a predetermined length, a flexible and resilient body installed in the longitudinal middle of said stretchable band, said flexible and resilient body being removably attached to said stretchable band whereby said flexible and resilient body becomes exchangeable, said flexible and resilient body having a portion of substantially triangular cross-section higher at one side than the other, the arrangement such that the higher portion of said flexible and resilient body is applied near the medial or lateral sole and the ankle can be fixed by being wrapped with said stretchable band. The flexible and resilient body may be made of any soft and bouncy material, preferably polyurethane sponge. In other embodiments of the invention, the flexible and resilient body is made from rubber, foam rubber, latex, elastic, or leather or other materials well known to those of ordinary skill in the art. The stretchable band may be made of materials well known to those of ordinary skill in the art such as elastic. The opposing ends of the stretchable band may be secured by means well known to those of ordinary skill in the art such as hooks and eyes, Velcro, buttons, or snaps.

In another embodiment of the invention, the arrangement of the therapeutic device is such that the portion of the stretchable band that extends in one direction is wrapped somewhat more tightly than the portion of the stretchable band that extends in the other direction. By observing the improvement of the symptoms, the intensity of wrapping of the right or left side of the ankle is suitably adjusted so as to achieve optimum therapeutic effect. In yet another embodiment, the arthritis is osteoarthritis. It is pleasant and easy to use, and may be worn over a bare foot, under a sock, and under open-toed shoes, boots, slippers and high-heels.

DETAILED DESCRIPTION OF THE INVENTION

Figure 1:
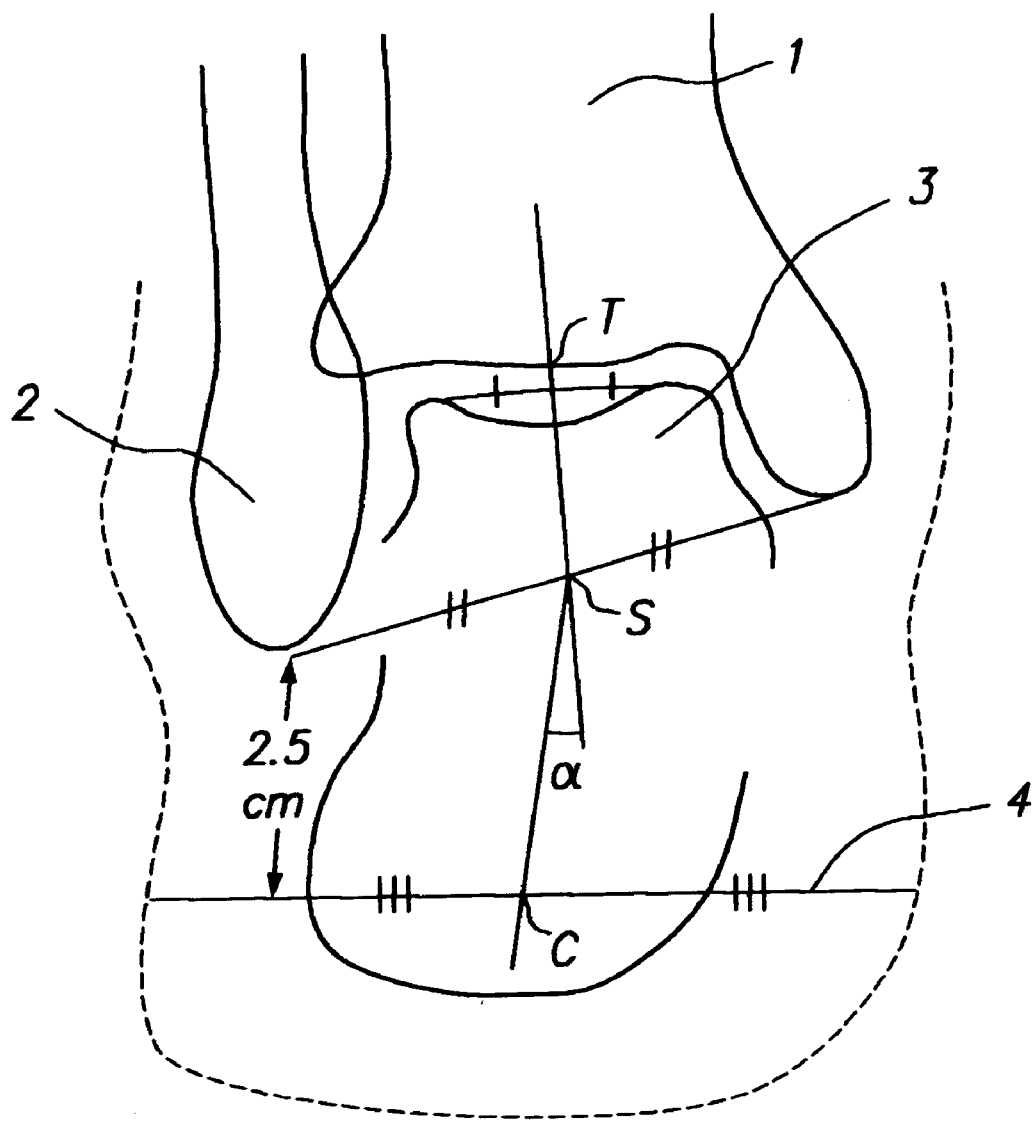
FIG. 1 is a conceptual view of the structure of an ankle demonstrating the spacial relationships of the tibia (1), fibula (2), talus (3) and parallel with the floor and 2.5 cms below the distal fibula.

A diagram of the ankle is provided as FIG. 1. Generally, an ideal ankle is considered to be one whose "T-point," "S-point" and "C-point" in FIG. 1 are arranged in a straight line and α-talocalcaneal angle=0°.

The T-point is the mid-point of a line connecting right and left convex ends of the upper edge of the talus trochanter.

The S-point is the mid-point of a line connecting the distal end of the fibula and the distal end of the tibia.

The C-point is the mid-point of a line parallel to the floor at a position 2.5-cm below the distal end of the fibula.

The direction of force in which the body weight acts is T-point->S-point and the direction in which a force resisting the gravity (gravity-resisting force) is C-point->S-point. As described above, the positioning of T-point, S-point and C-point in a straight line, α-talocalcaneal angle=0° is ideal. The greater the value of α-talocalcaneal, the greater the body weight that the knee joint and ankle must bear, and the greater the burden imposed on the knee joint and ankle.

According to the therapeutic device of the present invention, the positional relationship between the femur and the tibia can be restored to normal or substantially normal when the patient walks on a flexible and resilient body under the medial or lateral foot. This reduces local pressure on the cartilage between the femur and the tibia and alleviates symptoms, including pain, of arthritis of the knee.

According to the present invention, the body under the foot is used in conjunction with a stretchable band. The ankle is fixed by wrapping it with the stretchable band, whereby the aforesaid talocalcaneal angle, α, can be forcefully retained at substantially 0 (zero) degrees to further alleviate the symptoms, including pain, of arthritis of the knee. Clinical data is provided in the embodiments that follow.

Further, in the therapeutic device of the present invention, the stretchable band strip extends to the right and left of the flexible and resilient body, so that the therapeutic effect can be increased by wrapping either side more tightly than the other as symptoms warrant, so as to achieve maximal therapeutic effect.

In another embodiment, the therapeutic device of the present invention can be worn over a sock. This makes it possible to wear the article not only with ordinary shoes but continuously even while wearing open-toed shoes, boots, slippers, high-heels and if shoes are removed such as at home. The device is comfortable and easy for a patient to use, increasing patient compliance.

Since the flexible and resilient body is firmly fixed to the sole by attaching it to a stretchable band and wrapping said stretchable band around the flexible and resilient body, foot, and ankle as described above, the elastic body is stabilized and unlikely to become displaced during use.

The present invention offers a further advantage over other types of wedged insoles. Said flexible and resilient body is removably attachable to the stretchable band and can be easily removed or exchanged, washed, or replaced, according to circumstances; thus, it does not generally cause or aggravate foot odor. This also permits the replacement of a worn elastic body and the constant wear of the therapeutic device, which exhibits superior performance in correcting the displacement of the talocalcaneal joint. Further, the height of the flexible and resilient body can be easily adjusted in response to the progress of alleviation of the symptoms; thus, the article is very convenient and adjustable.

EMBODIMENTS

The preferred embodiment of the present invention is described in reference to the drawings. It is understood that the present invention is not limited to the particular methodology, protocols, material, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "and," and "the" include plural reference unless the context clearly dictates otherwise.

In addition, in the following description, the term "conventional sole plate" refers to an "insole with one of the right-hand and left-hand sides made in greater height than the other."

ARRANGEMENT OF THERAPEUTIC DEVICE

Figure 2:
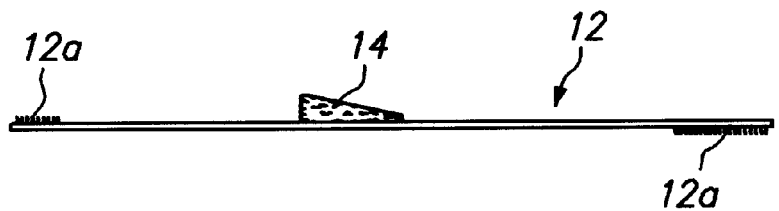
FIG. 2 is a side view of a therapeutic device according to a preferred embodiment of the invention demonstrating the stretchable band having a predetermined length (12); the flexible and resilient body installed in the longitudinal middle of said stretchable band (11), and fasteners (12a). In this embodiment, the fasteners are hooks and loops.
Figure 3:
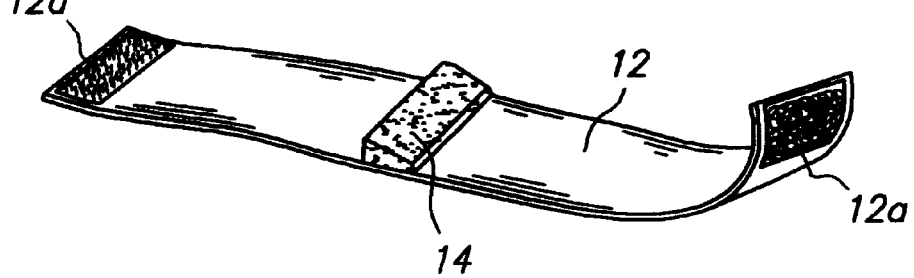
FIG. 3 is a view of the preceding figure as seen from above.

FIG. 2 is a side view of the present inventive therapeutic device (10), and FIG. 3 is a perspective view thereof. In the figures, the reference character (12) denotes a stretchable band which is, for example, 5–10 cm wide and 50–80 cm long (before stretching the maximum stretched length being, for example, 70–100 cm). The front surface of one end portion of the stretchable band (12) has the male part of a hook-and-loop fastener (12a) attached thereto, while the back surface of the other end portion has the female part of said hook-and-loop fastener (12a) attached thereto.

In addition, substantially the lengthwise middle of the stretchable band (12) has a flexible and resilient body (14) of soft polyurethane foam removably attached thereto.

Among the method for such removable attachment are one for attaching two parts by using a hook-and-loop fastener, and one for temporally fixing by sewing.

The flexible and resilient body (14), as illustrated, is substantially triangular in cross section, gradually increasing in thickness toward one end of the stretchable band (12) (or gradually decreasing in thickness toward the other end).

Figure 9A:
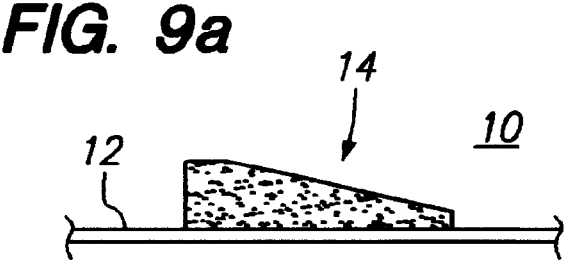
FIG. 9 is a partial view showing additional embodiments (a), (b), and (c), in which differently shaped flexible and resilient bodies (14) are employed.
Figure 9B:
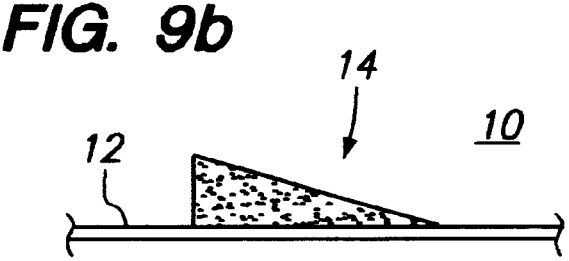
Figure 9C:
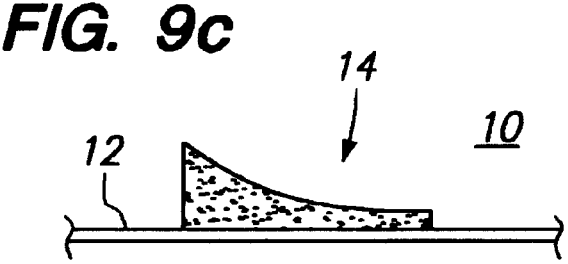

In addition, the shape of the flexible and resilient body (14) is not limited to the shape shown in the above embodiment (see FIG. 2); for example, a flexible and resilient body (14) having a portion of uniform thickness (see FIG. 9(a)), a flexible and resilient body (14) having a right triangular cross section in which one end of the upper surface of the flexible and resilient body (14) extends down to the upper surface of the stretchable band (12) (see FIG. 9(b)), or a flexible and resilient body (14) having a footrest of arcuate cross section (see FIG. 9(c)) may be employed, or other shapes may be employed.

Method of Treating Arthritis Using The Therapeutic Device

The method of treatment arthritis by applying the therapeutic device (10) of said arrangement is now be described.

Figure 4:
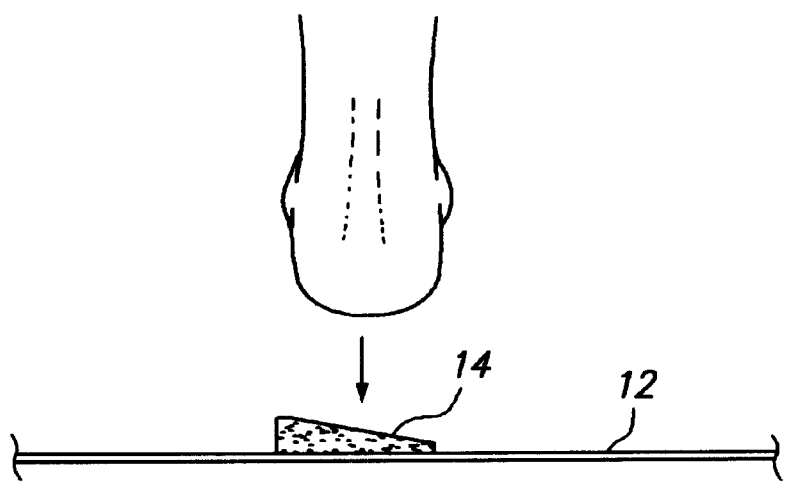
FIG. 4 is a view showing the therapeutic device of the invention in use, with a foot, observed posteriorly, being placed on the flexible and resilient body (14) in the therapeutic device (12).

First, as shown in FIG. 4, the therapeutic device (10) is placed on a floor to lie transversely. In this state, the foot is placed on the flexible and resilient body (14) directly from above. The placement of the higher portion, under the medial or lateral sole, should be on the side opposite the side of the knee that is experiencing pain. This means that if the medial knee aches, the higher side of the flexible and resilient body (14) should be under the lateral sole.

Figure 5:
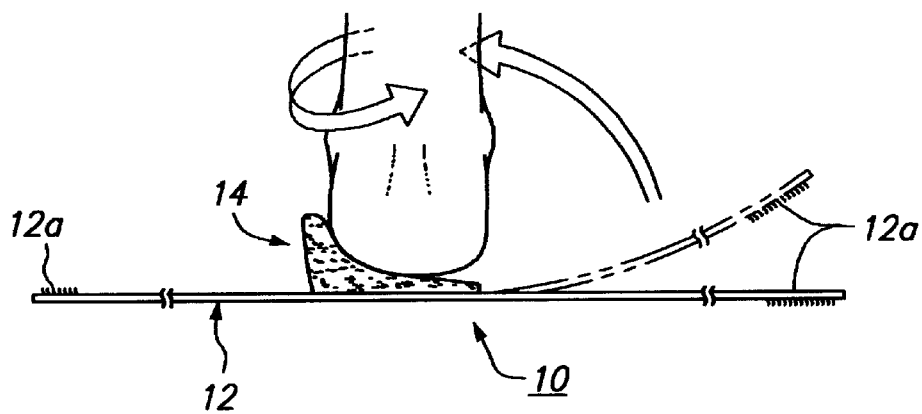
FIG. 5 is an explanatory view showing the posterior foot placed on the flexible and resilient body (14), with one end strip of the stretchable band (12) wrapped around the ankle.
Figure 6:
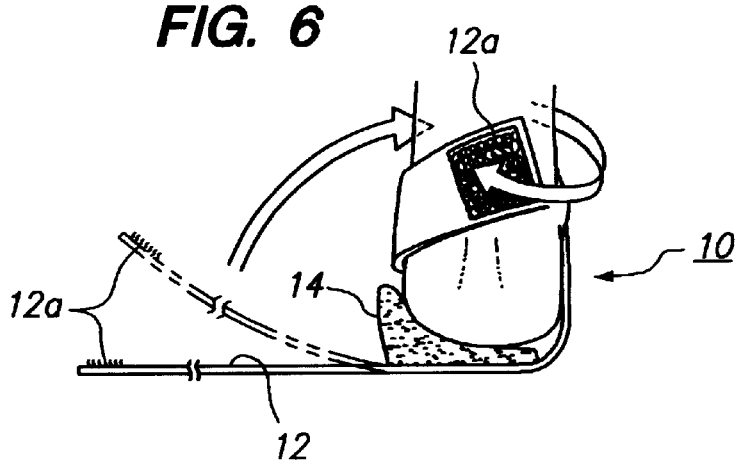
FIG. 6 is a explanatory view showing the other end strip of the stretchable band (12) wrapped around the ankle subsequent to the wrapping of one end strip of the stretchable band around the ankle.
Figure 7:
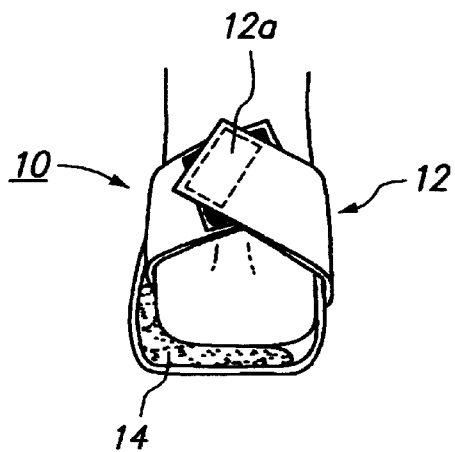
FIG. 7 is an explanatory view showing the posterior ankle, wrapped and fixed by the present inventive therapeutic device with the fasteners, shown in this embodiment as hooks and loops (12a), in contact with one another and secured.
Figure 8:
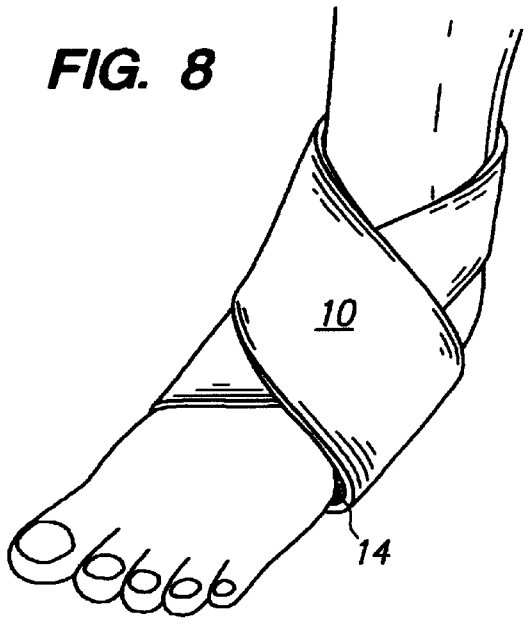
FIG. 8 is an explanatory anterior view of the preceding figure.

As shown in FIG. 5, with the foot placed on the flexible and resilient body (14), the flexible and resilient band (12) is wrapped around the ankle, and on the back of the ankle (just at the position of the Achilles' tendon), the right-hand and left-hand side strips of the stretchable band (12) are fastened together by the hook-and-loop fastener (12a). As shown in FIGS. 5–7, one end strip of the stretchable band (12) is held by hand and is moved from the anterior to posterior ankle and the other end strip is likewise moved in an anterior to posterior direction. The end strips are fastened at their overlapping portions by the hook-and-loop fastener (12a) at the position of the Achilles' tendon on the posterior ankle, as shown in FIG. 8. Thus, the ankle wrapped with the stretchable band (12) can be fixed by said stretchable band (12) with the foot placed on the flexible and resilient body (14).

Clinical Results

Patient 1: A 58-year old female patient suffering from osteoarthritis of long duration was asked to wear the present inventive therapeutic device, and the structural condition of her ankle was assessed by measuring the α-talocalcaneal angle by X-ray photography. See FIG. 1.

The result is shown in Table 1, below. Table 1 compares the condition of the disease in Patient 1 prior to wearing the present inventive therapeutic device, the condition of disease while wearing the present inventive device, and the condition of the disease while wearing the conventional sole plate.

TABLE 1

Patient 1 with Osteoarthritis of the Knee

|  | Left ankle | Right ankle |
| --- | --- | --- |
| Wearing nothing (control) (value of α-talocalcaneal angle) | 9° | 2° |
| Wearing inventive device (α value) | 2° | −1° |
| Wearing of conventional sole plate (α value) | 5° | 3° |

As is clear from the table 1, the present inventive therapeutic device brings the value of α-talocalcaneal angle is nearly 0°, providing a nearly ideal condition of the ankle. Thus, it can be fully expected that the burden of body weight on the knee is alleviated as compared with the conventional sole plate. In fact, this patient began to feel less pain in the knee about a week after wearing the present inventive therapeutic device, and the pain in the knee almost disappeared two weeks after.

A certain amount of correction is achieved with the conventional sole plate. However, as described above, such a sole plate is produced only after a mold has been produced, so that it is expensive. The one used in this clinical trial cost 6,000 yen. For this reason, it is thought that many patients will continue to use the sole plate even if the higher portion wears a little. When this occurs a certain amount of the correcting power and therapeutic effect is lost as time progresses and gradually disappears. Moreover, there is a danger of a reverse effect and worsening of the symptoms. In contrast, in the present inventive therapeutic device, the flexible and resilient body is constructed in such a way as to be replaceable with respect to the stretchable band. Even if the flexible and resilient body becomes worn, it is only necessary to replace such flexible and resilient body. Hence, a therapeutic device exhibiting a superior correcting power can be worn at all times. Further, the height of the flexible and resilient body can be easily adjusted in response to the progress of alleviation of the symptoms. The device is convenient and pleasant to use.

Clinical Result (2)

Nine (9) patients with osteoarthritis of the knee using conventional sole plates (insole type, both new and after one year of use), and 24 patients with osteoarthritis of the knee wearing the present inventive therapeutic device were studied. The structural condition of the ankle was assessed by measuring the α-talocalcaneal angle by X-ray photography as in the clinical result (1) above. The differences in the talocalcaneal angle, α, between patients standing on one foot wearing nothing, and wearing the conventional sole plate or the present inventive therapeutic article, changes in the α-talocalcaneal angle. Mean correction factors, showing that the greater the positive value, the greater the correction, were examined. The results are shown in FIG. 10.

Figure 10:
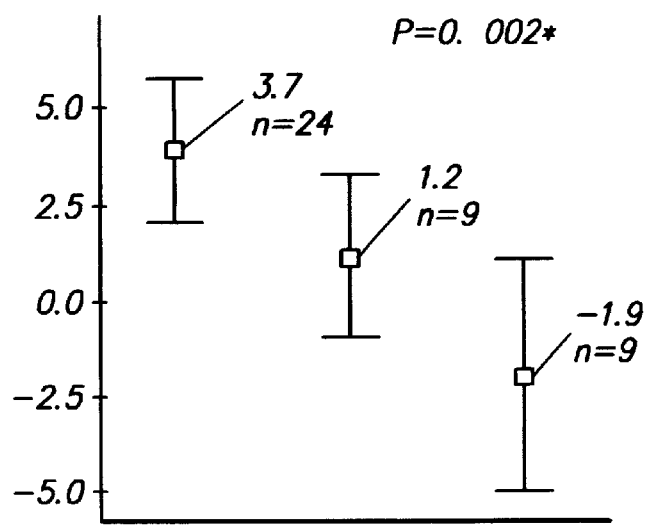
FIG. 10 is a graph showing changes, as mean difference in α-talocalcaneal angle between patients standing on one foot wearing the conventional sole plate or the present inventive therapeutic device, and standing on one foot without wearing said device.

As can be seen from the graph in FIG. 10, the mean difference in talocalcaneal angles between the control and treated values was 3.7° with the present inventive therapeutic article and 1.2° with the conventional sole plate when new. Thus, the present inventive therapeutic device can be expected to provide a greater therapeutic effect than the conventional sole plate even when the sole plate is new.

The conventional sole plate is expensive and tends to be used for many years, as described above. However, when one is used for one year, the sole plate conforms to the original foot shape and gradually loses its correcting power, thus showing a negative value of means correction factor of −1.9°.

Clinical Result (3)

Figure 11:
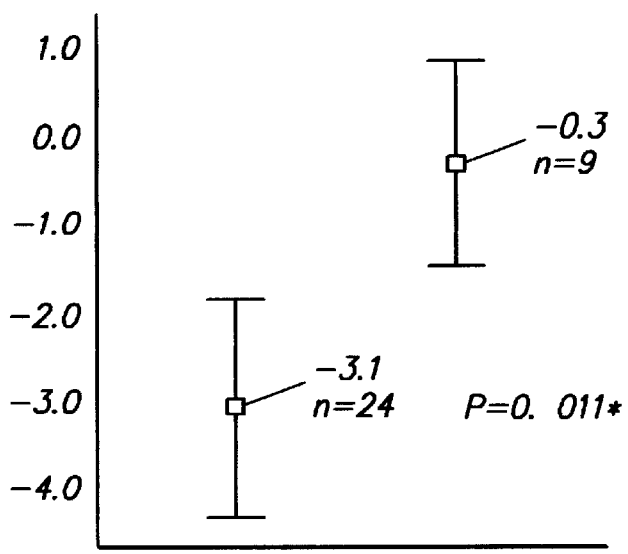
FIG. 11 is a graph showing changes at the femorotibial angle which is radiographic angle formed by the axes of the femur and the tibia, as mean values of knee correction angle (the greater the negative value, the greater the correction) between patients standing on one foot wearing the conventional sole plate or the present inventive therapeutic device and standing on one foot without wearing said device.

Nine (9) patients with osteoarthritis of the knee using conventional sole plates (insole type, both new and after one year of use), and 24 patients with osteoarthritis of the knee wearing the present inventive therapeutic device were studied. The change in the femorotibial angles was used to determine the knee correction angle. FIG. 11 depicts the differences in the knee correction angle, between patients standing on one foot wearing nothing, and wearing the conventional sole plate or the present inventive therapeutic device in changes in the knee corrective angle. The greater the negative value of the mean corrective angles, the greater the correction. The results are shown in FIG. 11.

As can be seen from the graph in FIG. 11, the mean corrective value for the angle of the knee, the difference between the control and treated values, was −3.1° with the present inventive therapeutic article and −1.2° with the conventional sole plate. Thus, the present inventive therapeutic device can be expected to provide a greater therapeutic effect than the conventional sole plate.

Clinical Result (4)

Twelve (12) patients with osteoarthritis of the knee complaining of pains with activities of daily living were asked to wear the present inventive therapeutic device every day, and changes in the severity of pain were examined before and after wearing. The results are shown in FIG. 12.

Figure 12:
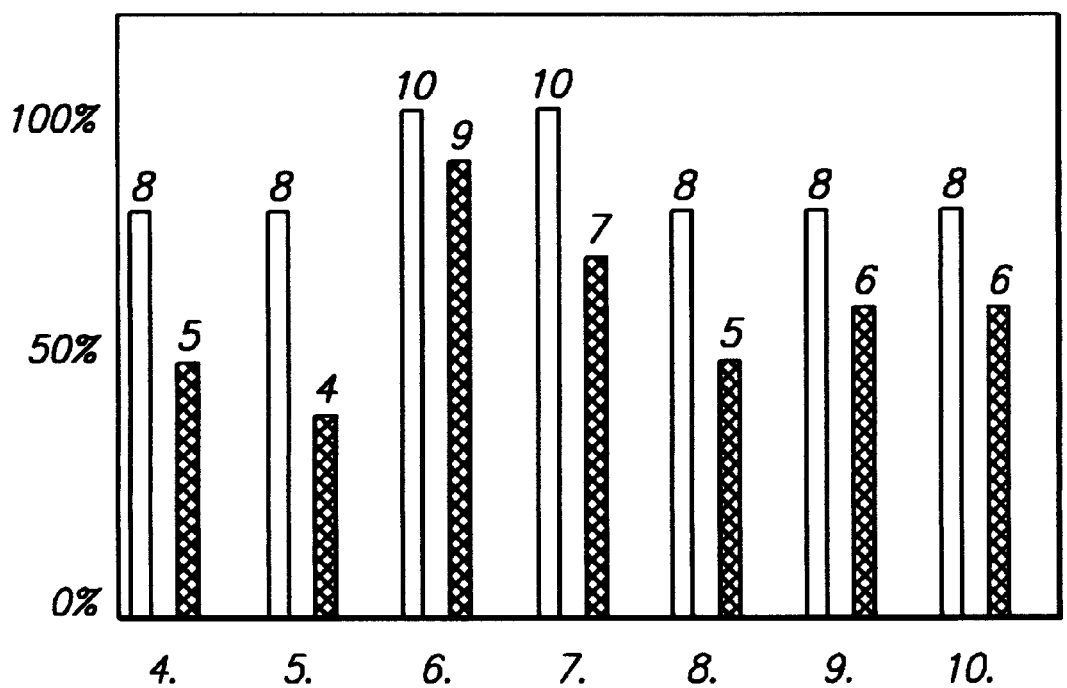
FIG. 12 is a graph showing changes in the severity of pain before and after wearing the present inventive therapeutic article while performing various activities.

As can be seen from FIG. 12, in each pain-inducing motion, the proportion of patients complaining of pains after wearing was reduced compared with that before wearing. Particularly, the number of patients complaining of pains in the knees when getting up, both when getting out of bed in the morning and when starting to move, was 8 (67%) before wearing, whereas after wearing, it was reduced by half to 4 (34%), which is a remarkable effect.

I claim:

1. A therapeutic device to treat arthritis of the knee comprising a means for fixating an ankle, said means for fixating being a subtalar strap, said subtalar strap having a predetermined length before stretching of 50–80 cm, a means for raising one side of the sole, said means for raising being a flexible, resilient body fastener to the center of said subtalar strap, said flexible, resilient body being thicker on one lateral side than the other lateral side, a means for fastening the device to a user, said means for fastening is a fastener attached to each end of the subtalar strap.

2. The therapeutic device of claim 1 wherein said flexible and resilient body is removably attached to said stretchable band, whereby said flexible and resilient body is exchangeable.

3. The therapeutic device of claim 1, wherein said arthritis of the knee is osteoarthritis.

4. The therapeutic device of claim 1, wherein said flexible and resilient body is comprised of polyurethane sponge.

5. The therapeutic device of claim 1, wherein said flexible and resilient body is comprised of rubber.

6. The therapeutic device of claim 1, wherein said flexible and resilient body is comprised of foam rubber.

7. The therapeutic device of claim 1, wherein said flexible and resilient body is comprised of latex.

8. The therapeutic device of claim 1, wherein said flexible and resilient body is comprised of elastic.

9. The therapeutic device of claim 1, wherein said flexible and resilient body is comprised of leather.

10. The therapeutic device of claim 1, wherein said flexible and resilient body has a portion of uniform height.

11. The therapeutic device of claim 1, wherein said flexible and resilient body has a right triangular cross section in which one end of the upper surface of the flexible and resilient body extends down to the upper surface of the stretchable band.

12. The therapeutic device of claim 1, wherein said flexible and resilient body has a footrest of arcuate cross section.

13. A method for reducing the talocalcaneal angle of a human arthritic knee comprising the steps of providing a subtalar strap comprising a stretchable band of a predetermined length and a flexible, resilient body, said body is thicker on one lateral side than the other lateral side, said flexible, resilient body is attached to the center of said subtalar strap, fasteners attached to the longitudinal ends on opposite ends of the subtalar strap, placing the foot of a human over the longitudinal middle of said subtalar strap such that said subtalar strap is under the arch of the human foot with its ends extending from the foot at perpendicular angles and said flexible, resilient body is below said subtalar strap, wrapping the longitudinal ends around the metatarsal of the human foot, causing said longitudinal ends to intersect over the dorsum of the human foot, wrapping said longitudinal ends around the ankle below the talus of the human foot, causing said longitudinal ends to intersect at the posterior ankle, fastening said longitudinal ends in place with said fasteners.

14. The method according to claim 13 wherein said arthritis is osteoarthritis.

15. The method according to claim 13 wherein said wrapping of the ankle with said stretchable band is used to fix the ankle.

16. The method according to claim 15 wherein said arthritis is osteoarthritis.

17. The method according to claim 15 wherein a portion of said stretchable band extending from one side of said flexible and resilient body is wrapped more or less tightly than the portion of said stretchable band extending from the other side of said flexible body in response to the progress of alleviation of the symptoms of arthritis.

18. The method according to claim 15 wherein the intensity of the wrapping of the right and left sides of the ankle are suitably adjusted to increase the therapeutic effect.

19. The method according to claim 13 wherein the strap and said body are worn over a sock.

20. The method according to claim 13 wherein the height of said flexible and resilient body is adjusted in response to the progress of the alleviation of symptoms of arthritis of the knee.

* * * * *